United States Patent [19]

Underwood

[11] 4,118,625

[45] Oct. 3, 1978

[54] NEPHELOMETER HAVING PULSED ENERGY SOURCE

[75] Inventor: Willie Bruce Underwood, Brandywine, Md.

[73] Assignee: Dynatech Laboratories Incorporated, Alexandria, Va.

[21] Appl. No.: 792,915

[22] Filed: May 2, 1977

[51] Int. Cl.² .............................................. G01N 21/26
[52] U.S. Cl. ................................................. 250/343
[58] Field of Search ................ 250/343, 373; 356/51, 356/103

[56] References Cited

U.S. PATENT DOCUMENTS

| 3,854,045 | 12/1974 | Breuer et al. | 250/343 X |
| 3,967,901 | 7/1976 | Rodriguez | 356/103 |

Primary Examiner—Davis L. Willis
Attorney, Agent, or Firm—Strauch, Nolan, Neale, Nies & Kurz

[57] ABSTRACT

A nephelometer that is insensitive to ambient light, characterized by the direction of very short pulses of energy at high frequency from an infrared laser to traverse a liquid containing suspended particles and the ability to detect, amplify and measure the peak values of pulses of energy scattered by particles traversed by the beam.

7 Claims, 2 Drawing Figures

U.S. Patent

Oct. 3, 1978

4,118,625

NEPHELOMETER HAVING PULSED ENERGY SOURCE

This invention relates to nephelometers and particularly to nephelometers characterized by ability to disregard ordinary ambient light sources, such as room lighting and sunlight, yet to respond in the desired manner to their own illumination source.

Basically in a nephelometer a beam of light traverses a liquid or other fluid and the scattering function of particles suspended in the fluid is detected and measured. One of the more serious problems encountered in these devices is the effect of ambient or spray light, and the art has developed considerable effort for shielding the detector against this unwanted light.

Figure 1:
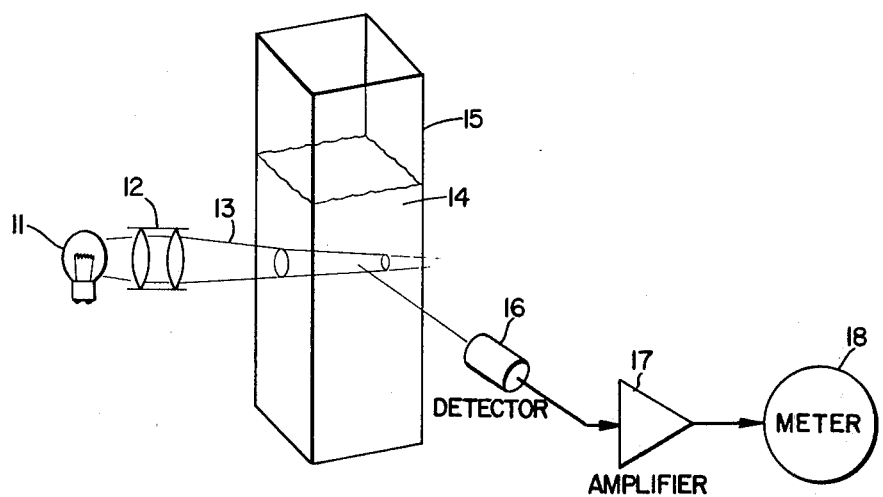

A typical nephelometer is shown in FIG. 1. Here a light source 11, generally an incandescent lamp, or in some cases a laser, is focused by a lens system 12 into a cone of light 13 which traverses a liquid medium 14 contained in a cuvette 15. When the cone of light within the medium is viewed at some angle to its path (usually about 90°) it will be visible only to the degree that light is scattered by the presence in the liquid medium of very small particles. These particles may be molecular in size and may consist of small organisms such as bacteria, etc.

The scattered light is detected by a photo-sensitive device 16 the electrical output of which amplified at 17 and displayed on a meter 18. The meter may be calibrated in units of turbidity.

This type of nephelometer is sensitive to light almost of any form which might illuminate the test medium or the photo-sensitive detector, thus requiring the entire apparatus to be protected from ambient light to avoid inaccuracies. Usually the cuvette holder has a light tight cover which must be fastened down over the test sample to prevent ambient light from entering the device.

The major object of the invention is to provide a novel nephelometer that accurately detects and measures light scattered by particles in a liquid medium with improved accuracy and without the need for shielding from ambient light.

It is an important object of the invention to provide a novel nephelometer wherein electromagnetic energy in the infrared spectrum and pulsed at high frequency traverses the liquid containing suspended particles and corresponding pulses of energy scattered by the particles are introduced into a system capable of accurately detecting the energy periodically scattered by the particles and usefully measuring that energy.

Pursuant to the foregoing object, the scattered pulses of infrared energy may be detected and converted to corresponding voltage pulses associated with a measuring system for determining the peak voltage incident to each pulse.

A further object of the invention is to provide a novel nephelometer wherein a beam of infrared energy pulses having a duration of between 20 and 200 nanoseconds and recurring at a period of between 1 and 2 milliseconds transverses a liquid containing particles to be evaluated and energy scattered by the particles is detected and usefully measured in a system utilizing a silicon diode detector having a response capability corresponding to the duration of the input energy pulses and producing corresponding pulsed voltage output impulses and an arrangement for measuring the peak values of the voltage impulses.

Further novel features and other objects of this invention will become apparent from the following detailed description, discussion and the appended claims taken in conjunction with the accompanying drawings.

FIG. 1 illustrates diagrammatically a prior art nephelometer.

Figure 2:
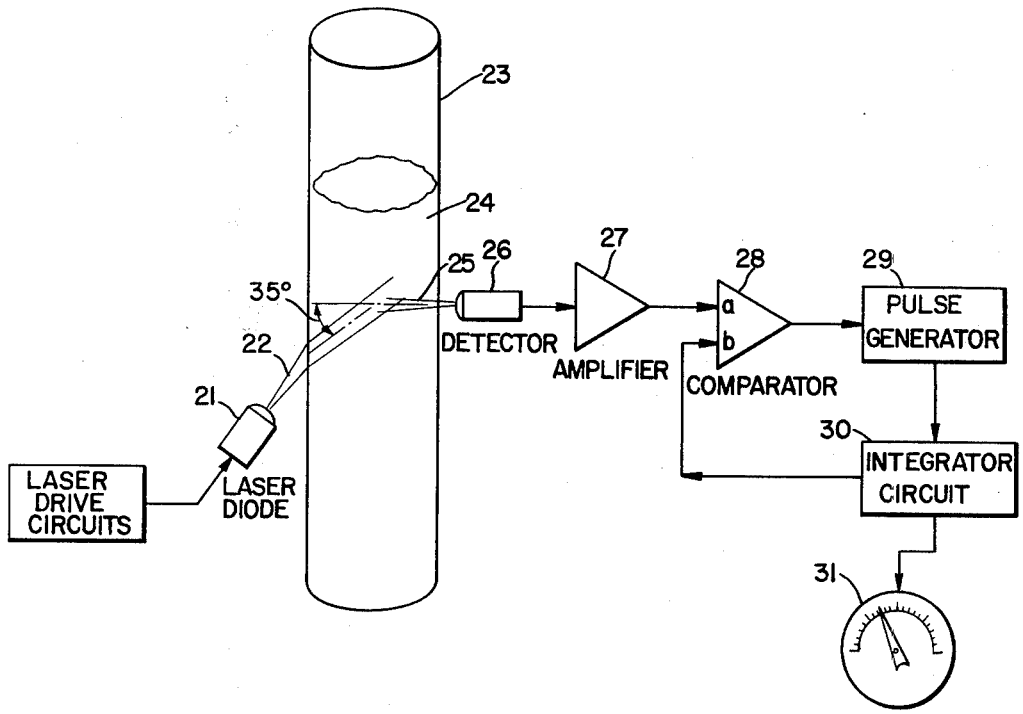

The nephelometer which is the subject of the invention is diagrammatically illustrated in FIG. 2.

An injection laser diode 21 is inergized for a period of approximately 100 nanoseconds respectively at a rate of approximately 1000 times per second.

Laser diode 21 emits a coherent beam in the form of a narrow cone 22 of infrared energy preferably nonochromatic or at least having a markedly dominant wave length which traverses a transparent test tube 23 at an angle of approximately 35° to the normal. Where the liquid test media 24 in the tube contains suspended particulate matter, such as bacteria, a certain amount of the infrared energy is forward scattered as indicated at 25 and the scattered energy detected by a photo-detector device 26 which preferably is a PIN diode that is highly sensitive to the dominant wavelength of the laser diode, and which can respond faithfully to extremely short pulses of received energy. Device 26 is preferably a silicon diode photo detector selected for its ability to respond to the very high frequency pulses of energy resulting from the high frequency periodic discharge from laser 21.

The electrical output response of silicon diode 26 is coupled through a high-pass filter (not shown) to a very high frequency amplifier stage 27.

The output of amplifier 27 is coupled to input $a$ of a high speed voltage comparator 28. When the instantaneous voltage at input $a$ exceeds the voltage at input $b$ of the comparator, the output of the comparator reverses, going from a positive output voltage to a negative output voltage. This negative-going voltage triggers a pulse generator 29 which produces an output pulse of approximately 500 microseconds duration, and this pulse turns on a solid-state switch which causes an integrating circuit 30 to acquire a small voltage. This small voltage is applied to input $b$ of comparator 29.

Thus each time the laser diode 21 fires, a pulse of energy is received by detector 26 and another increment of voltage is added in the integrator 30 until eventually the voltage at 30 and hence the voltage at input $b$ of comparator 28 builds up and exceeds the peak voltage amplitude of the pulse appearing at input $a$ of comparator 28. When this occurs, there is no output transition of comparator 28 and, consequently no output pulse from pulse generator 29. The voltage at integrator 30 slowly leaks down until the pulse amplitude at input $a$ of comparator 28 again exceeds the voltage at input $b$. At that point another increment voltage will be added at integrator 30. The voltage at integrator 30 will now very closely follow the peak amplitude of the voltage pulse from generator 29. A meter 31 is also coupled to receive and indicate the voltage at 30. The reading observed on the meter will be proportional to the degree of the infrared energy scattered by the test media, and the meter can be appropriately calibrated, as in terms of concentration.

The illuminator 21 is a solid-state injection laser diode emitting energy in the infrared region of the electromagnetic spectrum at a wave length within the range of 870 to 930 nanometers, and a particular laser diode successfully used with a silicon diode detector emits energy having a wave length of 903 nanometers. This latter wavelength is especially well suited to most phases of the invention for several reasons:

a. The liquid used in the test chamber is often amber colored. This amber color is seen as transparent at the preferred wavelength.
b. The purpose of this nephelometer in a present operative example is to measure the concentration of certain organisms suspended in a liquid by the degree to which these organisms scatter the illumination to which they are subjected. These particular organisms are relatively large in size. The longer wavelengths of invisible light, particularly the wavelength of 903 nanometers, is scattered quite well by these organisms.
c. This long wavelength (903 nm) is not present to any effective degree in normal room lighting, thus contributing to the overall insensitivity of this nephelometer to ambient light.
d. The 903 nanometer wavelength is near the area of best response for silicon photo-detectors of the type that are preferably used in this nephelometer because of their fast reliable response to high frequency short pulses of energy.

The most important advantage of this invention over other known nephelometers is the fact that it is totally insensitive to all usual ambient light sources, whether they be sunlight, incandescent lamps or fluorescent lamp. Even the direct beam of flashlight directed into the test specimen tube at close range has no ill effect.

The primary feature of this invention which makes it insensitive to ambient light is the combination of correlated elements providing the ability to generate, detect, amplify and measure the peak value of very short pulses of infrared energy down to 20 nanoseconds in time duration.

The sample holder for the medium may be a conventional test tube in lieu of the special tubes or cuvettes normally required in nephelometers. In the invention this tube does not require a light-tight cover so that the sample holder can be openly displayed without protection from ambient light and may be available for auxiliary operations, such as the adding of reagents, while the instrument is performing the turbidity measurement. Thus the effect of adding a drop of reagent while the test tube is in the nephelometer can be instantly observed in the test tube as well as at the nephelometer indicating meter.

Another advantage of this invention over other nephelometers is the fact that this invention uses less electrical energy for operation than other nephelometers. Other nephelometers usually illuminate the sample continuously during a test, whereas this invention illuminates for only 100 nanoseconds out of each millisecond or a ratio of 1 to 10,000. In other words, the illumination is turned on for only one ten thousands of the time. Since the illuminator consumes most of the power in the device, this invention uses less power than other nephelometers.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A nephelometer system for measuring the concentration of bacteria or other similar particulate material suspended in a liquid, said system comprising an infrared injection laser diode means for providing a pulsed beam of electromagnetic energy that is substantially monochromatic, said beam containing uniform repetitive energy pulses each having a short duration of between 20 and 200 nanoseconds, means for directing said beam through a liquid medium confined in a transparent vessel and containing a dispersion of the particles, means for detecting individual pulses of energy as foward scattered by said particles at an acute angle to said beam, and means for accurately measuring the peak amplitude of said detected pulses, said means of accurate measurement being capable of such measurement when the duration of said pulses is as short as 20 nanoseconds, and said short duration of pulses essentially enabling the system to perform its function in the presence of ambient light conditions such as daylight and artificial room lighting without the necessity of protecting the sample under test from said light.

2. In the nephelometer system defined in claim 1, said energy in the pulse beam having a dominant wave length in the range between 870 and 930 nanometers.

3. In the nephelometer system defined in claim 2, said detector being a silicon photo-detector, and said dominant wave length being about 903 nanometers.

4. In the nephelometer system defined in claim 1, said pulses being repeated at a period of from 1 to 2 milliseconds.

5. In the nephelometer system defined in claim 1, said acute angle being about 35°.

6. The nephelometer system defined in claim 1, wherein said detector incorporates a pulsed voltage output connected to one input of a high speed comparator the output of which is connected to a pulse generator that in turn is connected to an integrating circuit operatively connected to a meter and another input of said comparator, the foregoing detector components being so associated that whenever the peak value of the voltage received by said one input of the comparator is less than the voltage appearing at said other input, said pulse generator is actuated to supply an increment of voltage to said integrator circuit and the accumulated voltage at said integrator circuit is applied both to said meter and to said other input of the comparator, the combination of the foregoing correlated circuit elements coupled to the detector providing the capability to detect, amplify and accurately measure and display the peak values of repetitive pulses of infrared energy each having a duration as short as 20 nanoseconds.

7. In the nephelometer system defined in claim 1, said medium under test being confined in a transparent test tube unshielded from ambient light.

* * * * *